United States Patent [19]

Sandler

[11] Patent Number: 5,264,631
[45] Date of Patent: Nov. 23, 1993

[54] PROCESS FOR THE PREPARATION OF UNSYMMETRICAL ALKYL TRISULFIDES AND PRODUCTS

[75] Inventor: Stanley R. Sandler, Springfield, Pa.

[73] Assignee: Elf Atochem North America, Inc., Philadelphia, Pa.

[21] Appl. No.: 28,744

[22] Filed: Mar. 9, 1993

[51] Int. Cl.⁵ .......................................... C07C 319/20
[52] U.S. Cl. ..................................................... 568/21
[58] Field of Search .......................................... 568/21

[56] References Cited

U.S. PATENT DOCUMENTS 3,392,201  7/1968  Warner ................................. 568/26
4,564,709  1/1986  Koyama et al. ..................... 568/26

FOREIGN PATENT DOCUMENTS 885990  11/1971  Canada ................................. 253/97

OTHER PUBLICATIONS

T. Ghosh et al., J. Amer, Chem. Soc, 110, pp. 7499–7506 (1968).

Primary Examiner—Marianne M. Cintins
Assistant Examiner—Margaret J. Page

[57] ABSTRACT

A process is disclosed for the preparation of unsymmetrical dialkyl trisulfides by the reaction of dialkyl trisulfides and olefins in the presence of an acidic-type catalyst whereby alkyl groups are exchanged. Novel mixtures of symmetrical and unsymmetrical dialkyl trisulfides are also disclosed.

8 Claims, No Drawings

PROCESS FOR THE PREPARATION OF UNSYMMETRICAL ALKYL TRISULFIDES AND PRODUCTS

BACKGROUND OF THE INVENTION

This invention relates to the preparation of unsymmetrical alkyl trisulfides. More particularly, it relates to the reaction of an alkyl trisulfide with an olefin in the presence of an acidic-type catalyst to produce unsymmetrical alkyl trisulfides useful as extreme pressure additives in lubricating compositions.

THE PRIOR ART

It is well known to prepare symmetrical alkyl trisulfides by the reaction of mercaptans with sulfur, e.g., U.S. Pat. Nos. 3,392,201; 4,564,709 and Canadian Patent No. 885,990, utilizing specified conditions and catalysts.

An article by T. Ghosh and P.D. Bartlett, J. Amer. Chem Soc. 110, 7499-7506 (1988) discloses the reaction of phenyl substituted norbornenes or norbornadienes to give new trithiolanes by a trisulfide transfer reaction. No trisulfide transfer or donor properties with unsubstituted norbornanetrithiolanes were noted. A methyl substituted trithiolane gave no transfer reaction.

STATEMENT OF THE INVENTION

This invention is a process comprising reacting a terminal or internal branched olefin with a dialkyl trisulfide in the presence of an effective amount of an acidic-type catalyst for a time sufficient to produce an unsymmetrical trisulfide having an alkyl group of the trisulfide which is exchanged with said olefin, and the product of said process.

DETAILED DESCRIPTION OF THE INVENTION

The process of this invention involves the preparation of unsymmetrical dialkyl trisulfides and mixtures of symmetrical and unsymmetrical dialkyl trisulfides by reacting a dialkyl trisulfide with an olefin in the presence of an effective amount of a acidic catalyst.

The general scheme of the process is demonstrated by the following equations of alternatively useful reactions:

1) RS$_3$R$^1$ + 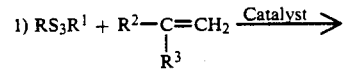 $\xrightarrow{\text{Catalyst}}$

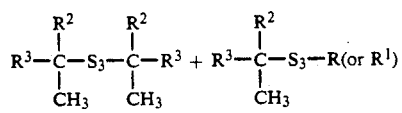

2) RS$_3$R$^1$ + 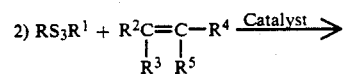 $\xrightarrow{\text{Catalyst}}$

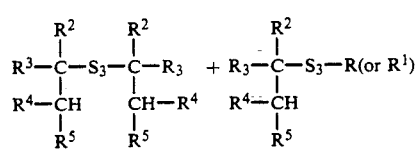

where R, R$^1$, R$^2$, R$^3$, R$^4$ and R$^5$ are the same or different alkyl groups preferably having from 1 to 20 carbons, provided that in equation 1) at least one of R and R$^1$ is different than the radical

and in equation 2) at least one of R and R$^1$ is different than the radical

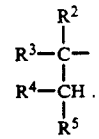

The catalyst is an acidic type.

The direct products of the reaction process of this invention are novel mixtures of symmetrical and unsymmetrical trisulfides, and usually a small amount of olefin, containing alkyl substituents differing from the starting olefin in percentage amounts varying, depending on the mole ratio of the reactants. The symmetrical trisulfide of the product will differ from the starting trisulfide by having different alkyl groups resulting from replacement with the olefin reactant. The symmetrical and unsymmetrical components may be separated, for example, by distillation, if desired.

The following is an equation for a typical reaction of this invention:

$(CH_3)_3CS_3C(CH_3)_3$ + $C_9H_{18}$ $\xrightarrow{\text{Acid Catalyst}}$ propylene trimer

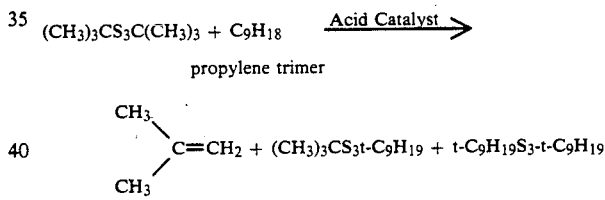

The process of this invention is carried out in either a batch or continuous operation at temperatures within the range of about 25° to 250° C., preferably between about 25° to 150° C. The pressure used for the reaction is not critical and is generally between atmospheric and 1000 psig, preferably between 0 to 100 psig. The reaction time is also not critical so long as the alkyl group exchange is accomplished and, for a batch process, generally extends between 1 and 24 hours, preferably from 1 to 8 hours.

The reactants may be present in the reaction process at a mole ratio of trisulfide to olefin ranging from 1:1 to 1:10 depending on the ratio of products desired. To prepare a product having a predominant amount of unsymmetrical trisulfide, a mole ratio of trisulfide to olefin is 1:1 to about 1:2; for a product with a high proportion of symmetrical trisulfide incorporating transferred alkyl groups, a mole ratio of 1:3 to about 1:6 is preferred.

The alkyl trisulfide reactant is generally a symmetrical dialkyl trisulfide preferably having from 1 to 20 carbon atoms including, for example, methyl, ethyl, propyl, isopropyl, butyl, isobutyl, secondary butyl, tertiary (t)-butyl, pentyl, isopentyl, t-pentyl, hexyl, isohexyl, t-hexyl, heptyl, octyl, isooctyl, nonyl, t-nonyl, decyl, dodecyl, t-dodecyl, tetradecyl, pentadecyl, hexadecyl, octadecyl, eicocyl and alkyl isomers of these.

The trisulfide may be derived in situ from a di-t-alkyl polysulfide of higher sulfur rank than said trisulfide which polysulfide may dissociate under the conditions of the reaction resulting in the presence of di-t-alkyl trisulfides.

The olefins included within the process of this invention are terminal and internal branched olefins. The terminal olefin contains alkyl groups (R) on the double bond. Examples of useful olefins are:

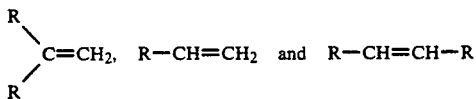

For example 4- vinyl-1-cyclohexene, d-limonene, 2-methyl-1-hexene, 1-methyl-1-cyclohexene, propylene trimer, and the like.

The catalysts which are used with this invention are the acidic type including acidic ion-exchange materials of the resin based and non resin based type; organic acids, e.g., carboxylic and sulfonic acids; inorganic acids such as the mineral acids, phosphoric acid silicotungstic, phosphotungstic and arsenic acid, as well as Lewis acids such as boron trifluoride aluminum chloride and zinc chloride. Preferably, the acid catalyst is one that is readily separated from the reaction mixture. Examples of easily separated catalyst are the acidic ion-exchange resins. One particularly preferred catalyst is Amberlyst ® 15, a strongly acidic, cation exchange resin, sold by Rohm & Haas, having an—$SO_3H$ functional structure and a macroreticular form. The catalyst used is a beaded resin, preferably in the anhydrous state. Other acidic ion exchange resins are also available and include, for example, the Amberlite ®200 series sold by Rohm & Haas and Dowex ® 50 sold by Dow Chemical.

The catalyst is used in the process of this invention in effective amounts, i.e., amounts which will promote or increase the rate of the reaction. Preferably, the catalyst is used in an amount ranging from about 50 g to about 155 g based on each mol of trisulfide. The catalyst can be recycled, especially if it is a resin catalyst, and leave no contamination in the reaction mixture.

The following examples are set forth to demonstrate the merits of this invention.

EXAMPLE 1

To a reactor was added 0.21 g (0.001 mole) of di-t-butyl trisulfide, 0.26 g (0.002 mole) of propylene trimer ($C_9H_{18}$) and 0.12 g Amberlyst ® 15 acid catalyst. The mixture was warmed at 80°-90° C. and occasionally shaken for about 5 hours to give a mixture of t-butyl, t-nonyl trisulfide (15.3%) and di-t-nonyl trisulfide (3.2%). The result of the reaction was confirmed by gas chromatography and mass spectroscopy analyses.

To a reactor was added 0.19 g (0.0009 mole) of di-t-butyl trisulfide and 0.275 g (0.0022 mole) of propylene trimer (no catalyst). The mixture was warmed at 80°-90° C. and occasionally shaken for about 5 hours to give only a trace of reaction as confirmed by analyses using gas chromatography.

To a reactor was added 0.193 g (0.00092 mole) of di-t-butyl trisulfide and 0.275 (0.0022 mole) of propylene trimer and 0.182 g. Amberlyst ® A-21 (tertiary amine functionality, weakly basic ion exchange resin from Rohm & Haas Co.). The mixture was warmed at 80°-90° C. and occasionally shaken for about 5 hours to give only a trace of reaction (about no better than comparative Example A without catalyst) as confirmed by analyses using gas chromatography.

EXAMPLE 2

To a reactor was added 0.21 g (0.001 mole) of di-t-butyl trisulfide, 0.19g (0.002 mole) of 1-methylcyclohexene and 0.12g Amberlyst ® 15 acid catalyst. The mixture was warmed at 80°-90° C. and occasionally shaken for about 2 hours to give a mixture of t-butyl 1-methylcyclohexyl trisulfide (16.2%) and di-1-methylcyclohexyl trisulfide (3.1%). The result of the reaction was confirmed by gas chromatography and mass spectroscopy analysis.

The above examples demonstrate the value of the process of this invention. The process permits greater versatility for the preparation of trisulfides than the prior art method. Symmetrical alkyl trisulfides having alkyl groups for which mercaptans containing such groups are not readily available, may be prepared from inexpensive olefins in accordance with this process. Additionally, unsymmetrical trisulfides not heretofore readily available can be easily prepared by this method. The only reference for a trisulfide transfer reaction known by the inventor from the prior art (as disclosed hereinbefore) is one disclosing a process for preparing cyclic trisulfides (norbornanetrithiolanes) which requires a phenyl substituent as an activating group to be present for the trisulfide transfer to be effected (Ghosh and Bartlett)

The products of this invention are mixtures of symmetrical and unsymmetrical $C_1$-$C_{20}$ alkyl trisulfides, preferably mixtures wherein the symmetrical trisulfide is a tertiary dialkyl trisulfide. The symmetrical components are present in amounts within the range of from 5 to 95% based on the weight of the mixture, as are the unsymmetrical components.

I claim:

1. A process for producing an unsymmetrical dialkyl trisulfide comprising reacting a terminal or internal branched olefin with a dialkyl trisulfide in the presence of an effective amount of an acidic-type catalyst for a time sufficient to produce an unsymmetrical dialkyl trisulfide having an alkyl group exchanged with said olefin.

2. The process of claim 1 wherein the dialkyl trisulfide reactant is a symmetrical dialkyl trisulfide.

3. The process of claim 1 wherein said olefin contains at least one tertiary alkyl group.

4. The process of claim 1 wherein the reaction is conducted at a temperature within the range of about 25° to 250° C.

5. The process of claim 4 wherein the reaction is conducted at a pressure between about atmospheric and 1000 psig for about 1 to about 24 hours.

6. The process of claim 5 wherein the mole ratio of dialkyl trisulfide to olefin is from 1:1 to 1:10.

7. The process of claim 1 wherein the acidic-type catalyst is a strongly acidic, cation exchange resin of the macroreticular type.

8. A process for producing an unsymmetrical dialkyl trisulfide in mixture with a symmetrical dialkyl trisulfide comprising reacting a $C_1$-$C_{20}$ symmetrical dialkyl trisulfide with an olefin having at least one tertiary alkyl group in its structure at a mole ratio of about 1:2 to about 1:6, at a temperature ranging from about 25 to about 150° C., a pressure of about 0 to about 100 psig and for a time of from about 1 to about 8 hours in the presence of a strongly acidic, cation exchange resin of the macroreticular type in an amount of from 50 to 155 grams based on each mol of trisulfide.

* * * * *